US012577229B2

(12) United States Patent
Richards

(10) Patent No.: US 12,577,229 B2
(45) Date of Patent: Mar. 17, 2026

(54) SUBSTITUTED {5-METHOXY-6-[(5-METHOXYPYRIDIN-2-YL)METHOXY]PYRIDIN-3-YL} METHYL COMPOUNDS AS CSF-1R INHIBITORS

(71) Applicant: Eli Lilly and Company, Indianapolis, IN (US)

(72) Inventor: Simon James Richards, Hannington (GB)

(73) Assignee: Eli Lilly and Company, Indianapolis, IN (US)

( * ) Notice: Subject to any disclaimer, the term of this patent is extended or adjusted under 35 U.S.C. 154(b) by 708 days.

(21) Appl. No.: 17/997,258

(22) PCT Filed: Apr. 23, 2021

(86) PCT No.: PCT/US2021/028773

§ 371 (c)(1),
(2) Date: Oct. 27, 2022

(87) PCT Pub. No.: WO2021/225798

PCT Pub. Date: Nov. 11, 2021

(65) Prior Publication Data

US 2023/0167086 A1 Jun. 1, 2023

Related U.S. Application Data

(60) Provisional application No. 63/020,093, filed on May 5, 2020.

(51) Int. Cl.
*C07D 401/14* (2006.01)
*A61P 25/28* (2006.01)

(52) U.S. Cl.
CPC .................................. *C07D 401/14* (2013.01)

(58) Field of Classification Search
CPC .................................................... C07D 401/14
See application file for complete search history.

(56) References Cited

U.S. PATENT DOCUMENTS 11,992,535 B2 * 5/2024 Liu ...................... C07D 401/12

FOREIGN PATENT DOCUMENTS

| | | |
|---|---|---|
| WO | 2011/150198 | 12/2011 |
| WO | 2014/001802 | 1/2014 |

OTHER PUBLICATIONS

International Search Report of PCT/US2021/028773 (filed Apr. 23, 2021 by Eli Lilly and Company), Search completed on Jun. 11, 2021, Mailed on Jun. 25, 2021 by the European Patent Office, 5 pages.

International Written Opinion of PCT/US2021/028773 (filed Apr. 23, 2021 by Eli Lilly and Company), Search completed on Jun. 11, 2021, Mailed on Jun. 25, 2021 by the European Patent Office, 6 pages.

* cited by examiner

*Primary Examiner* — Bruck Kifle
*Assistant Examiner* — Kevin S Martin
(74) *Attorney, Agent, or Firm* — Gabriel Magallanes

(57) ABSTRACT

The present invention provides a compound of Formula I: Formula I or a pharmaceutically acceptable salt thereof, to pharmaceutical compositions comprising the compound and to methods of using the compound to treat physiological disorders.

Formula I

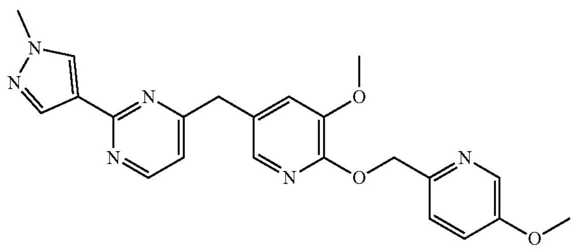

8 Claims, No Drawings

SUBSTITUTED {5-METHOXY-6-[(5-METHOXYPYRIDIN-2-YL)METHOXY]PYRIDIN-3-YL} METHYL COMPOUNDS AS CSF-1R INHIBITORS

The present invention relates to a novel substituted {5-methoxy-6-[(5-methoxypyridin-2-yl)methoxy]pyridin-3-yl}methyl compound, to pharmaceutical compositions comprising the compound and to methods of using the compound to treat physiological disorders.

The present invention is in the field of treatment of Alzheimer's disease and other diseases and disorders involving microglia-mediated inflammation.

Alzheimer's disease is a devastating neurodegenerative disorder that affects millions of patients worldwide. In view of the current approved agents on the market, which afford only transient, symptomatic benefits to the patient, there is significant unmet need in the treatment of Alzheimer's disease.

Elevated microglial expression and associated neuroinflammation are regarded as playing key roles in both Alzheimer's disease initiation and progression (Hemonnot et al., *Frontiers in Aging Neuroscience,* 11, 233, 1-19 (2019)). Colony stimulating factor-1 receptor (CSF-1R) is a class III receptor tyrosine kinase activated by two homodimeric glycoprotein ligands, CSF-1 and IL-34. It is expressed on all microglia and it directly controls their development and maintenance (Chitu et al., *Trends Neurosci.,* 39(6), 378-393 (2017)). Recent studies (Olmos-Alonso et al., *Brain,* 139, 891-907 (2016)) have shown that inhibition of microglial proliferation by inhibition of CSF-1R ameliorates disease progression in the APP/PS1 model of Alzheimer's disease. Reductions in intraneuronal amyloid, neuritic plaque formation and pre-fibrillar and fibrillar oligomers with concomitant improvements in cognitive function in the 5xFAD model of Alzheimer's disease were observed with administration of the CSF-1R inhibitor PLX3397 (Sosna et al., *Molecular Neurodegen.,* 13, 11, 1-11 (2018)). In addition, the CSF-1R inhibitor JNJ-40346527 has been shown to inhibit tau phosphorylation and aggregation in the P301S mouse tauopathy model (Mancuso et al., *Brain,* 142, 3243-3264 (2019)). Accordingly, CSF-1R inhibitors are an accepted approach for the prevention of plaque formation and the reduction of the accumulation of hyperphosphorylated, pathological forms of tau in animal models.

Furthermore, microglia-mediated inflammation has been associated with disorders such as progressive supranuclear palsy (PSP) (Fernandez-Botran et al., *Parkinsonism Relat. Disord.,* 17, 9, 683-688 (2011)), Parkinson's disease (PD) (Tansey and Goldberg, *Neurobiol. Dis.,* 37, 3, 510-518 (2010)), amyotrophic lateral sclerosis (ALS) (Liu et al., *Front. Immunol.,* 8, 1005, 1-12 (2017)), primary lateral sclerosis (PLS) (Paganoni et al., *NeuroImage: Clinical,* 17, 347-353 (2018)), multiple sclerosis (MS) (Beckmann et al., *Acta Neuropathologica Commun.,* 6:9, 1-17 (2018)), peripheral neuropathic pain (Inoue et al., *Nat. Rev. Neurosci.,* 19, 138-152 (2018)), central neuropathic pain (Lee et al., *Mol. Pain,* 14, 1-12 (2018)) and age-related sarcopenia and mobility deficits in the elderly (Giorgetti et al., *Cell Reports,* 29, 1539-1554 (2019)). Historically, CSF-1R inhibitors have been investigated for use in the treatment of various types of cancer and autoimmune diseases (Kumari et al., *Biomed. Pharmacother.,* 103, 662-679 (2018)).

Meyers et al., *Bioorg. Med. Chem. Lett.,* 20, 1543-1547 (2010) discloses 3-amino-6-(1-methyl-1H-pyrazol-4-yl) pyrazin-2-ol derivatives as CSF-1R kinase inhibitors.

Consequently, there is a need for potent, selective, and/or brain-penetrant CSF-1R inhibitors for the treatment of Alzheimer's disease, or diseases and disorders involving microglia-mediated inflammation in human beings.

The present invention provides certain novel compounds that are inhibitors of CSF-1R.

Accordingly, the present invention provides a compound of Formula I:

Formula I

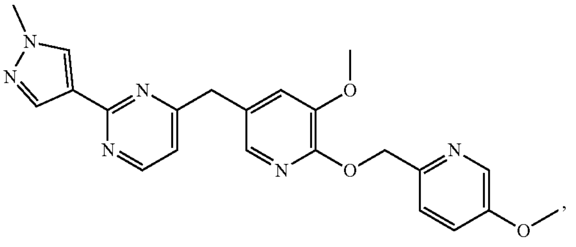

or a pharmaceutically acceptable salt thereof.

In an embodiment, the present invention further provides a compound of Formula I:

Formula I

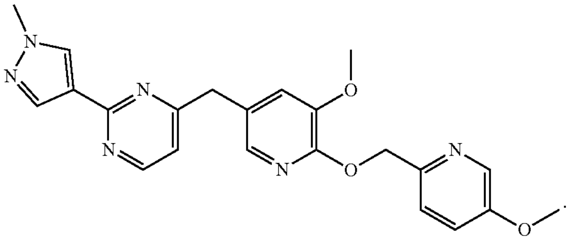

The present invention also provides a method of treating Alzheimer's disease in a patient in need of such treatment, comprising administering to the patient an effective amount of a compound of Formula I, or a pharmaceutically acceptable salt thereof.

The present invention further provides a method of preventing the progression of mild cognitive impairment to Alzheimer's disease in a patient in need of such treatment, comprising administering to the patient an effective amount of a compound of Formula I, or a pharmaceutically acceptable salt thereof.

The present invention also provides a method of treating progressive supranuclear palsy in a patient, comprising administering to a patient in need of such treatment an effective amount of a compound of Formula I, or a pharmaceutically acceptable salt thereof.

The present invention also provides a method of treating tau-mediated neurodegenerative disorders in a patient, comprising administering to a patient in need of such treatment an effective amount of a compound of Formula I, or a pharmaceutically acceptable salt thereof.

The present invention further provides a method of treating a disease or disorder involving microglia-mediated inflammation, comprising administering to a patient in need of such treatment an effective amount of a compound of Formula I, or a pharmaceutically acceptable salt thereof.

The present invention also provides a method of treating a disease or disorder selected from Parkinson's disease, amyotrophic lateral sclerosis, multiple sclerosis, primary lateral sclerosis, peripheral neuropathic pain, central neuropathic pain and age-related sarcopenia, comprising administering to a patient in need of such treatment an effective amount of a compound of Formula I, or a pharmaceutically acceptable salt thereof.

Furthermore, this invention provides a compound of Formula I, or a pharmaceutically acceptable salt thereof, for use in therapy.

The present invention also provides a compound of Formula I, or a pharmaceutically acceptable salt thereof, for use in the treatment of Alzheimer's disease.

The present invention further provides a compound of Formula I, or a pharmaceutically acceptable salt thereof, for use in the prevention of the progression of mild cognitive impairment to Alzheimer's disease.

The present invention also provides a compound of Formula I, or a pharmaceutically acceptable salt thereof, for use in the treatment of progressive supranuclear palsy.

The present invention also provides a compound of Formula I, or a pharmaceutically acceptable salt thereof for use in the treatment of tau-mediated neurodegenerative disorders.

The present invention further provides a compound of Formula I, or a pharmaceutically acceptable salt thereof, for use in the treatment of a disease or disorder involving microglia-mediated inflammation.

The present invention also provides a compound of Formula I, or a pharmaceutically acceptable salt thereof, for use in the treatment of a disease or disorder selected from Parkinson's disease, amyotrophic lateral sclerosis, multiple sclerosis, primary lateral sclerosis, peripheral neuropathic pain, central neuropathic pain and age-related sarcopenia.

Even furthermore, the invention provides the use of a compound of Formula I, or a pharmaceutically acceptable salt thereof, for the manufacture of a medicament for the treatment of Alzheimer's disease or for preventing the progression of mild cognitive impairment to Alzheimer's disease. In addition, the invention also provides the use of a compound of Formula I, or a pharmaceutically acceptable salt thereof, for use in the treatment of progressive supranuclear palsy. Furthermore, the invention provides the use of a compound of Formula I, or a pharmaceutically acceptable salt thereof, for the manufacture of a medicament for treating tau-mediated neurodegenerative disorders. In addition, the invention also provides the use of a compound of Formula I, or a pharmaceutically acceptable salt thereof, for use in the treatment of a disease or disorder involving microglia-mediated inflammation. Furthermore, the invention also provides the use of a compound of Formula I, or a pharmaceutically acceptable salt thereof, for use in the treatment of a disease or disorder selected from Parkinson's disease, amyotrophic lateral sclerosis, multiple sclerosis, primary lateral sclerosis, peripheral neuropathic pain, central neuropathic pain and age-related sarcopenia.

The invention further provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients.

In an embodiment, the present invention provides a method of treating cancer in a patient, comprising administering to the patient in need of such treatment an effective amount of a compound of Formula I, or a pharmaceutically acceptable salt thereof. In an embodiment, the cancer is selected from: glioma, pancreatic cancer, breast cancer or acute myeloid leukemia. In an embodiment, the glioma is glioblastoma multiforme. In a further embodiment, the present invention provides a method of treating an autoimmune disease in a patient, comprising administering to the patient in need of such treatment an effective amount of a compound of Formula I, or a pharmaceutically acceptable salt thereof. In an embodiment, the autoimmune disease is rheumatoid arthritis.

Mild cognitive impairment has been defined as a potential prodromal phase of dementia associated with Alzheimer's disease based on clinical presentation and on progression of patients exhibiting mild cognitive impairment to Alzheimer's dementia over time. The term "preventing the progression of mild cognitive impairment to Alzheimer's disease" or "prevention the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art by the use of known techniques. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.1 to about 15 mg/kg of body weight. In some instances, dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

The compounds of the present invention, or pharmaceutically acceptable salts thereof, may be prepared according to the following Preparations and Examples by methods well known and appreciated in the art. Suitable reaction conditions for the steps of these Preparations and Examples are well known in the art and appropriate substitutions of solvents and co-reagents are within the skill of the art.

Likewise, it will be appreciated by those skilled in the art that synthetic intermediates may be isolated and/or purified by various well-known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, and is well appreciated by the skilled chemist. All substituents, unless otherwise indicated, are as previously defined, and all reagents are well known and appreciated in the art.

Certain abbreviations are defined as follows: "BSA" refers to bovine serum albumin; "CSF-1R" refers to colony stimulation factor-1 receptor; "DCM" refers to dichloromethane or methylene chloride; "DMEM" refers to Dulbecco's Modified Eagle's Medium; "DMF" refers to N,N-dimethylformamide; "DMSO" refers to dimethyl sulfoxide; "EGTA" refers to ethylene glycol tetraacetic acid; "ES/MS" refers to electrospray ionization mass spectroscopy; "EtOAc" refers to ethyl acetate; "EtOH" refers to ethyl alcohol or ethanol; "FBS" refers to Fetal Bovine Serum; "HEPES" refers to 4-(2-hydroxyethyl)-1-piperazineethanesulfonic acid; "hCSF-1R" refers to human Colony stimulation factor 1 receptor; "$IC_{50}$" refers to the concentration of an agent which produces 50% of the maximal inhibitory response possible for that agent (relative $IC_{50}$), or the concentration of an agent which produces 50% inhibition of the target activity compared to placebo control (absolute $IC_{50}$); "IPTG" refers to isopropyl β-D-1-thiogalactopyranoside; "LC/MS" refers to liquid chromatography mass spectroscopy; "M-C SF" refers to macrophage colony-stimulating factor; "MeOH" refers to methanol or methyl alcohol; "MP-TMT" refers to macroporous polystyrene-bound trimercaptotriazine, a resin bound equivalent of 2,4,6-trimercaptotriazine; "m/z" refers to mass to charge ratio; "PBS" refers to Phosphate Buffered Saline; "pCSF-1R" refers to phosphorylated colony stimulation factor 1 receptor; "PDGFRβ" refers to platelet derived growth factor receptor beta; "PDGF-BB" refers to platelet derived growth factor-2 B subunits; "RT" refers to room temperature; "SCX" refers to strong cation exchange chromatography; "SFC" refers to supercritical fluid chromatography; "TEA" refers to triethylamine; "TFA" refers to trifluoroacetic acid; and "THF" refers to tetrahydrofuran.

In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977). "Salt selection for basic drugs," *International Journal of Pharmaceutics,* 33: 201-217 (1986). One of ordinary skill in the art will appreciate that a compound of Formula I is readily converted to and may be isolated as a pharmaceutically acceptable salt.

PREPARATIONS AND EXAMPLES

The following Preparations and Examples further illustrate the invention.

Preparation 1

Ethyl 2-chloropyrimidine-4-carboxylate

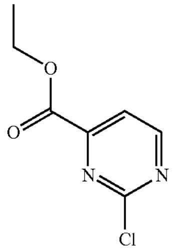

Oxalyl chloride (309 mL, 3557 mmol) is added slowly over 1 hour to a suspension of 2-chloropyrimidine-4-carboxylic acid (470.0 g, 2964.6 mmol) in mixture of DCM (5 L) and DMF (10 mL). The suspension is stirred at ambient temperature for 1 hour and then cooled to 0° C. A solution of EtOH (1.05 L) in DCM (1.4 L) is slowly added and the mixture is stirred for 30 minutes at 10° C. Saturated aqueous sodium hydrogen carbonate (2.5 L) is slowly added and the layers are separated. The aqueous is extracted with DCM (5 L) and the organic extracts are combined, washed with brine (2×4 L), dried over sodium sulfate, filtered, and evaporated to give a solid residue. The residue is slurried in n-heptane (2.5 L), filtered and dried under vacuum to give the title compound as a yellow solid (493.5 g, 89%). ES/MS m/z ($^{35}Cl/^{37}Cl$) 187.0/189.0 $[M+H]^+$.

Preparation 2

4-Methyl-2-(1-methylpyrazol-4-yl)pyrimidine

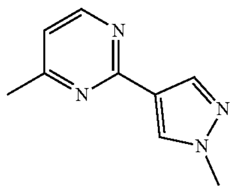

2-Chloro-4-methyl-pyrimidine (20 g, 155.57 mmol), 1-methyl-4-(4,4,5,5-tetramethyl-1,3,2-dioxaborolan-2-yl)-1H-pyrazole (40 g, 182.633 mmol), bis(triphenylphosphine) palladium(II) dichloride (2.7 g, 3.8 mmol), potassium carbonate (87 g, 616.89 mmol), 1,4-dioxane (250 mL), and water (80 mL) are added together under a nitrogen atmosphere. The solution is nitrogen/vacuum purged (3×) and heated to 100° C. with stirring for 20 hours. The reaction is poured into saturated ammonium chloride (about 500 mL), and the product is extracted with EtOAc (about 3×200 mL). The organic extracts are dried over magnesium sulphate, filtered, and concentrated in vacuo to give a black oil which is then purified by silica gel flash chromatography eluting with a gradient of 100% hexanes to 100% EtOAc to give the title compound as an orange solid (26.379 g, 97% yield, 151.43 mmol). ES/MS m/z 175 (M+H).

Preparation 3

Ethyl 2-(1-methylpyrazol-4-yl)pyrimidine-4-carboxylate

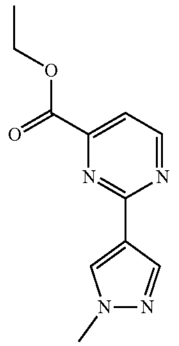 [SMILES: CCOC(=O)c1ccnc(-c2cnn(C)c2)n1]

Ethyl 2-chloropyrimidine-4-carboxylate (493.0 g, 2642.0 mmol), 1-methyl (4,4,5,5tetramethyl-1,3,2-dioxaborolan-2-yl)pyrazole (770.0 g, 3700 mmol), bis(triphenylphosphine) palladium(II) dichloride (55.63 g, 79.26 mmol), and potassium fluoride (465.0 g, 7924.0 mmol) are combined in 1,4-dioxane (5 L) and water (1.23 L) and purged with nitrogen for 20 minutes. The mixture is heated to 82° C. (internal temperature) for 19 hours. The mixture is cooled to ambient temperature and diluted with EtOAc (5 L). The layers are separated, and the organic layer is washed with water (5 L). The aqueous layer is extracted with EtOAc (5 L) and the organic extracts are combined, dried over sodium sulfate, filtered, and evaporated to dryness to give a pale yellow solid. The residue is slurried in heptane (2.5 L), filtered, washed with heptane (2.5 L) and dried under vacuum to give the title compound as a pale yellow solid (455.0 g, 73%) ES/MS m/z 233.0 (M+H).

Preparation 4

[2-(1-Methylpyrazol-4-yl)pyrimidin-4-yl]methanol

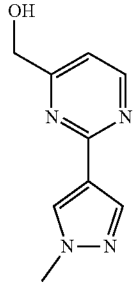

Sodium borohydride (109.0 g, 2881.1 mmol) is added portionwise to a solution of ethyl 2-(1-methylpyrazol-4-yl) pyrimidine-4-carboxylate (452.0 g, 1926.8 mmol) in EtOH (6.3 L) and TFA (1.35 L) maintaining the internal temperature below 25° C. and the mixture is stirred until LC/MS shows a complete reaction. 15% aqueous potassium hydrogen sulfate (6 L) is added and then tert-butyl methyl ether (5 L) is added and any precipitated solids are removed by filtration. The layers are separated and the aqueous is extracted with tert-butyl methyl ether (5 L). The organic extracts are combined and concentrated to about a 2 L volume. This mixture is extracted with 15% aqueous potassium hydrogen sulfate until the product is fully extracted from the organic phase. The pH is adjusted to pH 12 with portionwise addition of solid potassium carbonate. The aqueous material is extracted with 2-methyl tetrahydrofuran (4×7.5 L), dried over sodium sulfate filtered and evaporated to dryness to give the title compound as a pale yellow solid (251.0 g, 67%). ES/MS m/z 191.0 (M+H). Two other batches of the title compound are prepared in a similar manner to give the title compound as pale yellow solid (18.0 g and 114.3 g). The combined material is triturated with heptane (2.5 L), filtered and dried under house vacuum to give the title product as a pale yellow solid (371 g, 1911.6 mmol). MS (m/z) 191 (M+H).

Preparation 5

4-(Chloromethyl)-2-(1-methylpyrazol-4-yl)pyrimidine

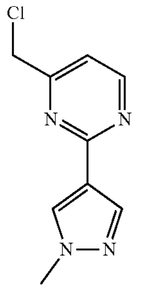

[2-(1-Methylpyrazol-4-yl)pyrimidin-4-yl]methanol (100 g, 525.76 mmol) is added to DCM (1 L) under nitrogen giving a white slurry. The slurry is cooled to 0° C. and TEA (144 mL, 1030 mmol) is added dropwise over 3 minutes. Methanesulfonyl chloride (60 mL, 773 mmol) is added dropwise over 50 minutes and an exotherm is observed. The internal temperature is maintained below 8° C. During the addition the reaction mixture gradually turned red, then returned to yellow at the end of the addition. Once the addition is complete the reaction mixture is heated to 38° C. under $N_2$ for 5 hours. The reaction mixture is cooled to 8° C. under nitrogen and TEA (25 mL, 179 mmol) is added followed by dropwise addition of methanesulfonyl chloride (10 mL, 129 mmol) over 5 minutes (mild exotherm observed). The reaction mixture is then refluxed overnight. The mixture is cooled and treated with water (1 L). The phases are separated and the aqueous is extracted with DCM (0.5 L). The organic extracts are combined, dried over magnesium sulfate, filtered, and the solvent evaporated to give a brown oil. The crude oil is dissolved in DCM (250 ml), filtered through a pad of silica, and washed with EtOAc (1 L). The filtrate is evaporated to give a brown solid (92.6 g, 444 mmol, 84.4%). MS (m/z) 209 (M+H).

Preparation 6

2-(1-Methylpyrazol-4-yl)pyrimidine-4-carbaldehyde

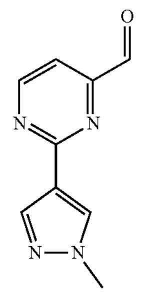

4-Methyl-2-(1-methylpyrazol-4-yl)pyrimidine (10.00 g, 57.41 mmol), selenium dioxide (7.6 g, 66 mmol), 1,4-dioxane (110 mL), and water (5.7 mL) are added together. The mixture is heated to 100° C. with stirring for 20 hours to give a black solution. The reaction cooled, filtered through diatomaceous earth, and washed with THF (about 100 mL). The filtrate and washings are combined and concentrated in vacuo. Chloroform (about 150 mL) is added and the resulting solid is filtered and collected. The solid is further washed with chloroform (about 50 mL) and filtered. The combined filtrates are concentrated to about 30 mL volume and purified by silica gel flash chromatography eluting with a gradient of 100% hexanes to 100% EtOAc to give a light-yellow solid as the title compound (4.550 g, 42% yield, 24.18 mmol). ES/MS m/z 189/207 (M+H/M+18).

Preparation 7

4-Methyl-N-[(E)-[2-(1-methylpyrazol-4-yl)pyrimidin-4-yl]methyleneamino]benzenesulfonamide

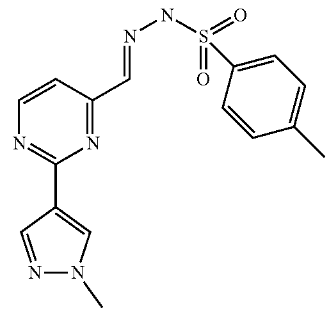 [SMILES: Cc1ccc(S(=O)(=O)N/N=C/c2ccnc(-c3cnn(C)c3)n2)cc1]

2-(1-Methylpyrazol-4-yl)pyrimidine-4-carbaldehyde (4.550 g, 24.18 mmol) is added to MeOH (60 mL) followed by 4-methylbenzenesulfonhydrazide (5.05 g, 26.6 mmol) and the mixture is stirred for 2 hours. The mixture is cooled to 0° C., filtered, and the resulting solid is washed with MeOH (about 20 mL). The solid is dried in vacuo to give the title compound as a white solid (7.229 g, 84% yield, 20.28 mmol). ES/MS m/z 357 (M+H).

Preparation 8

2-Benzyloxy-5-bromo-3-methoxy-pyridine

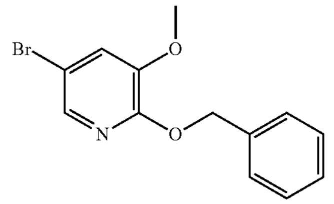 [SMILES: COc1cc(Br)cnc1OCc1ccccc1]

5-Bromo-2-chloro-3-methoxy-pyridine (14.5 g, 65.2 mmol), phenylmethanol (7.4 mL, 72 mmol), and potassium tert-butoxide (9.5 g, 85 mmol) are added together with 1,4-dioxane (200 mL) under nitrogen and heated to 50° C. for 2 hrs. The reaction mixture is cooled to room temperature and poured onto saturated aqueous ammonium chloride solution (350 mL). The product is extracted with EtOAc (2×300 mL), dried over magnesium sulphate, filtered, and concentrated in vacuo. The crude residue is purified by silica gel chromatography, Combiflash®, eluting with 100% hexanes to 50% EtOAc to give the title compound as a white solid (16.53 g, 56.19 mmol, 86%). ES/MS m/z ($^{79}$Br/$^{81}$Br 294/296 (M+H)$^+$.

Preparation 9

5-Bromo-3-methoxy-2-[(5-methoxy-2-pyridyl)methoxy]pyridine

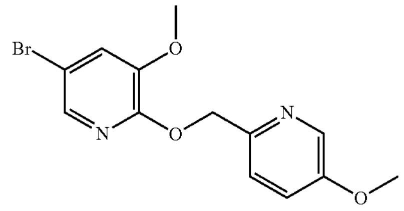 [SMILES: COc1ccc(COc2ncc(Br)cc2OC)nc1]

The following procedure is based on procedure described in J. Org. Chem. 2008, 73, 6425-6428. Potassium tert-butoxide (212 g, 1851.50 mmol) is added portionwise to a solution of 5-bromo-2-chloro-3-methoxy-pyridine (323 g, 1422.8 mmol) and (5-methoxy-2-pyridyl)methanol (200 g, 1422.9 mmol) in 1,4-dioxane (4 L) at 2θ° C. under a nitrogen atmosphere. The mixture is heated to 50° C. for 1 hr and then cooled to ambient temperature before adding a solution of saturated aqueous ammonium chloride (500 mL). The resulting precipitate is removed by filtration, washed with EtOAc and the filtrate is evaporated to give a brow residue. The residue is dissolved in DCM and passed through a plug of silica gel (1 kg), eluting with EtOAc/n-heptane (1:1). The desired fractions are isolated, evaporated to dryness and slurried in n-heptane (5 L). The slurry is heated to 80° C. and then cooled to ambient temperature. The resulting solids are collected by filtration, washed with n-heptane and dried in a vacuum oven at 45° C. to obtain the title compound as an off-white solid (413.5 g, 88%). ES/MS m/z 325.0/327.0 [M+H].

Preparation 10

(6-Benzyloxy-5-methoxy-3-pyridyl)boronic acid

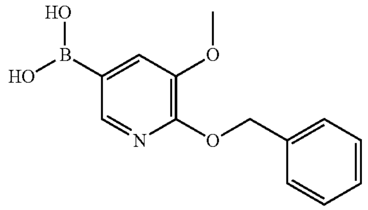 [SMILES: COc1cc(B(O)O)cnc1OCc1ccccc1]

Toluene (300 mL) is cooled to −78° C. under nitrogen and N-butyllithium (2.5 mol/L) in hexanes (40 mL, 100 mmol) is added dropwise keeping temperature below −65° C. A solution of 2-benzyloxy-5-bromo-3-methoxy-pyridine (25.7 g, 87 mmol) in toluene (150 mL) is added dropwise ensuring temperature is kept below −60° C. and the solution is stirred for 40 minutes. THF (150 mL) is added dropwise to the reaction keeping the temperature below −60° C. and the mixture is stirred for 10 minutes. Triisopropyl borate (25 mL, 108 mmol) is added dropwise over 2 minutes, and the reaction is allowed to warm to 10° C. with stirring. The reaction is poured onto saturated ammonium chloride solution (500 mL) and extracted with EtOAc (2×200 mL). The extracts are dried over magnesium sulphate, filtered, and concentrated in vacuo. Diethyl ether (200 mL) is added to the residue and the mixture is sonicated for 5 minutes and then filtered. The solid is washed with further diethyl ether (100 mL) and dried in vacuo to give the title compound as a white solid (8.99 g, 34.71 mmol, 40%). ES/MS m/z 260 [M+H].

Preparation 11

3-Methoxy-2-[(5-methoxy-2-pyridyl)methoxy]-5-(4,4,5,5-tetramethyl-1,3,2-dioxaborolan-2-yl)pyridine

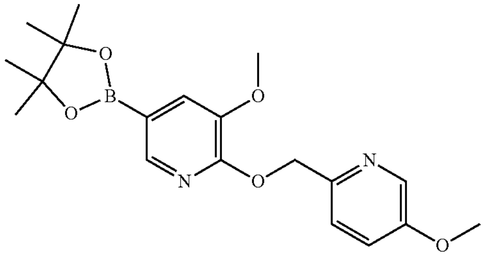

1,4-Dioxane (6.15 L), 5-bromo-3-methoxy-2-[(5-methoxy-2-pyridyl)methoxy]pyridine (413.5 g, 1259 mmol), 4,4,5,5-tetramethyl-2-(4,4,5,5-tetramethyl-1,3,2-dioxaborolan-2-yl)-1,3,2-dioxaborolane (360.2 g, 1390 mmol), bis(triphenylphosphine)palladium(II) dichloride (8.9 g, 13 mmol), potassium acetate (376 g, 3792.88 mmol) are added together under a nitrogen atmosphere and the solution is sparged with nitrogen for 15 min. The reaction mixture is heated to 100° C. until LCMS indicates complete conversion of starting material. The solution is cooled to 25° C. and the reaction mixture is filtered through a plug of diatomaceous earth, eluting with EtOAc (2.5 L) and evaporating the solvent to obtain a black solid. The residue is purified by passing through a plug of silica (1 Kg) eluting with 1:1 EtOAc/n-heptane (10 L) followed by EtOAc (10 L) and evaporating the purified material to dryness. The purified material is slurried in cyclopentyl methyl ether/n-heptane (1:1, 5 L) at 30° C. and the resulting precipitate is collected by filtration to give the title compound as a grey solid (393.9 g, 83%). ES/MS m/z 373.2 [M+H].

Preparation 12

4-[(6-Benzyloxy-5-methoxy-3-pyridyl)methyl]-2-(1-methylpyrazol-4-yl)pyrimidine

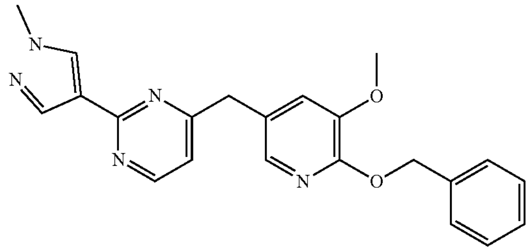 [SMILES: CN/C=C(\C=N)c1nccc(Cc2cnc(OCc3ccccc3)c(OC)c2)n1]

(6-Benzyloxy-5-methoxy-3-pyridyl)boronic acid (4.00 g, 15.4 mmol), 4-methyl-N-[(E)-[2-(1-methylpyrazol-4-yl)pyrimidin-4-yl]methyleneamino]benzenesulfonamide (5.5 g, 15 mmol), potassium phosphate (8.3 g, 39 mmol), and 1,2-dichlorobenzene (120 mL) are added together. The mixture is flushed with nitrogen and heated to 150° C. with stirring for 10 hours and then cooled to RT overnight. The reaction is then heated to 170° C. for 5 hours and is poured into saturated ammonium chloride solution (about 250 mL). The mixture is extracted with EtOAc (2×200 cm3), the organic extracts are dried over magnesium sulphate, filtered, and concentrated in vacuo. The residue is purified silica gel chromatography, Combiflash®, eluting with 100% DCM to 50% DCM/THF to give the title compound as a yellow solid (3.15 g, 8.12 mmol, 53%). ES/MS m/z 388 [M+H].

Preparation 13

3-Methoxy-5-[[2-(1-methylpyrazol-4-yl)pyrimidin-4-yl]methyl]pyridin-2-ol

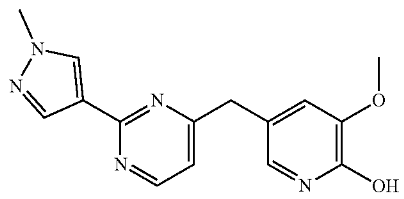 [SMILES: COc1cc(Cc2ccnc(-c3cnn(C)c3)n2)cnc1O]

4-[(6-Benzyloxy-5-methoxy-3-pyridyl)methyl]-2-(1-methylpyrazol-4-yl)pyrimidine (3.147 g, 8.123 mmol) is added to DCM (15 mL) followed by TFA (15 mL) addition. The reaction is stirred for 150 minutes and then concentrated in vacuo. The reaction is carefully poured into saturated sodium bicarbonate solution (about 80 mL) and extract with 2:1 $CHCl_3$/EtOH (about 6×30 mL). The organic extracts are dried over magnesium sulphate, filtered, and concentrated in vacuo. The residue is purified by silica gel chromatography, Combiflash®, eluting with 100% DCM to 85% DCM/MeOH to give the title compound as a light yellow solid (2.523 g, 8.486 mmol, 100%). ES/MS m/z 298 [M+H].

EXAMPLE 1

4-({5-Methoxy-6-[(5-methoxypyridin-2-yl)methoxy]pyridin-3-yl}methyl)-2-(1-methyl-1H-pyrazol-4-yl)pyrimidine

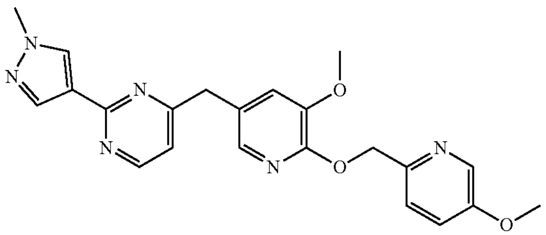 [SMILES: COc1ccc(COc2ncc(Cc3ccnc(-c4cnn(C)c4)n3)cc2OC)nc1]

3-Methoxy-5-[[2-(1-methylpyrazol-4-yl)pyrimidin-4-yl]methyl]pyridin-2-ol (0.1 g, 0.336 mmol), (5-methoxy-2-pyridyl)methanol (0.1 g, 0.719 mmol), and THF (3.5 mL) are added together. Triphenylphosphine (0.18 g, 0.160 mL, 0.686 mmol) and diisopropyl azodicarboxylate (0.13 mL, 0.656 mmol) are added to the reaction. The vessel is sealed, flushed with nitrogen, and stirred for 1 hour. The reaction is diluted with MeOH and poured onto a SCX2 column. The column is flushed with one column volume of MeOH and is eluted with one column volume flush of 2 M methanolic ammonia followed by concentration in vacuo. The residue is purified by SFC using Column PPU 3 cm i.d.×15 cm (5 μ) at 55° C. and eluting with a gradient of 15-25% MeOH (40 mM ammonia) in 4 mins (6 minute method) at 100 mL/min to give the title compound as a yellow oil (0.0097 g, 0.023 mmol, 7%). ES/MS m/z 419 [M+H].

Alternative Preparation Example 1

4-({5-Methoxy-6-[(5-methoxypyridin-2-yl)methoxy]pyridin-3-yl}methyl)-2-(1-methyl-1H-pyrazol-4-yl)pyrimidine

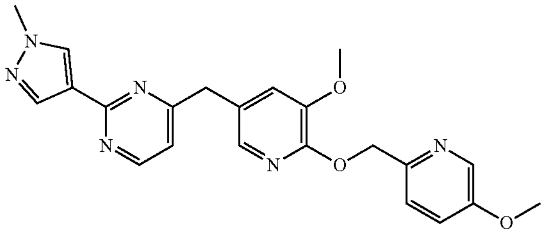 [SMILES: COc1ccc(COc2ncc(Cc3ccnc(-c4cnn(C)c4)n3)cc2OC)nc1]

3-Methoxy-2-[(5-methoxy-2-pyridyl)methoxy]-5-(4,4,5,5-tetramethyl-1,3,2-dioxaborolan-2-yl)pyridine (150 g, 399.0 mmol) in 1,4-dioxane (375 mL, 4392 mmol) and THF (1.075 L) is sparged with nitrogen and added under nitrogen atmosphere to solution of 4-(chloromethyl)-2-(1-methylpyrazol-4-yl)pyrimidine (83.4 g, 396 mmol), dichloro[1,1'-bis(di-tert-butylphosphino)ferrocene]palladium(II) (5.25 g, 8.06 mmol), potassium phosphate monohydrate (386.4 g, 1594 mmol) in 1,4-dioxane (1.2 L) and water (300 mL) and heated to 80° C. (total addition time 80 min). After an additional 15 min, the reaction is cooled to ambient temperature and diluted with water (2.5 L) and 2-methyltetrahydrofuran (2.5 L). The organic layer is separated and washed with water (2×2.5 L). The aqueous layer is extracted with 2-methyl tetrahydrofuran (2.5 L) and the organic extracts combined, dried with magnesium sulfate, filtered, and evaporated to a gummy residue. The residue if filtered through silica gel (1 kg) eluting with EtOAc followed by 5% MeOH in DCM. The desired fractions are collected and evaporated to dryness, dissolved in DCM and stirred with MP-TMT (25 g) at 25° C. under a nitrogen atmosphere. The resin is removed by filtration and purified by silica gel flash column chromatography eluting with a gradient of with 0-5% MeOH in DCM. the purified product containing fractions are evaporated and dissolved in THF (1.15 L). The solution is warmed to 50° C. and n-heptane (1.5 L) is slowly added until the solution becomes cloudy. The solution is heated to 65° C. and THF (500 mL) is slowly added to dissolve the slurry and obtain a clear solution. The mixture is cooled to 0° C. and the resulting solids are collected by vacuum filtration and dried to obtain the title compound (101.7 g, 60%) as a white solid. ES/MS m/z 419.0 [M+H].

EXAMPLE 2

4-({5-Methoxy-6-[(5-methoxypyridin-2-yl)methoxy]pyridin-3-yl}methyl)-2-(1-methyl-1H-pyrazol-4-yl)pyrimidine; dihydrochloride

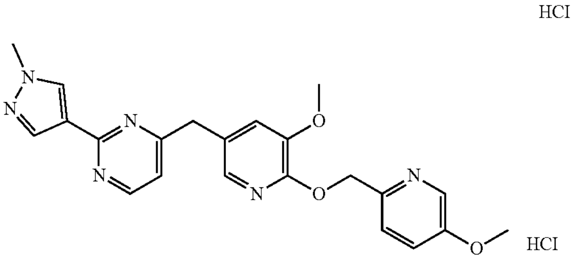

4-({5-Methoxy-6-[(5-methoxypyridin-2-yl)methoxy]pyridin-3-yl}methyl)-2-(1-methyl-1H-pyrazol-4-yl)pyrimidine (257 mg) is dissolved in acetone (5 mL) to give a clear pale-yellow solution. To the mixture, hydrochloric acid (1.4 mL; 1M in EtOAc) is introduced to precipitate a white solid. The suspension is stirred for 15 minutes and diluted with acetone (10 mL). The reaction mixture is filtered and the solid dried under nitrogen stream at ambient temperature to give the title compound as a crystalline solid. ES/MS m/z 419 [M+H].

EXAMPLE 3

4-({5-Methoxy-6-[(5-methoxypyridin-2-yl)methoxy]pyridin-3-yl}methyl)-2-(1-methyl-1H-pyrazol-4-yl)pyrimidine (Crystalline Form A)

Form A

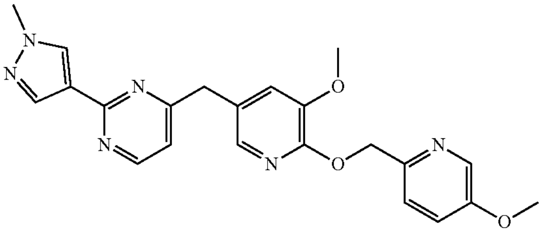

EtOAc (250 mL) and 4-({5-methoxy-6-[(5-methoxypyridin-2-yl)methoxy]pyridin-3-yl}methyl)-2-(1-methyl-1H-pyrazol-4-yl)pyrimidine (10 g) are charged to a flask. The reaction is heated to 40~50° C. and stirred for 4-6 hours. The reaction mixture is filtered and diluted with EtOAc. The mixture is cooled to 10° C., stirred for 12 hours, filtered and the solids rinsed with EtOAc. The solid is dried at T≤50° C. to give the title compound as a crystalline solid (90% yield). ES/MS m/z 419.0 [M+H].

EXAMPLE 4

4-({5-Methoxy-6-[(5-methoxypyridin-2-yl)methoxy]pyridin-3-yl}methyl)-2-(1-methyl-1H-pyrazol-4-yl)pyrimidine (Crystalline Form B)

Form B

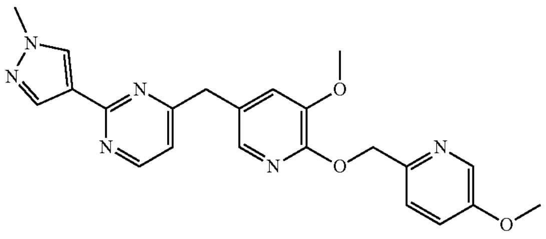

4-({5-Methoxy-6-[(5-methoxypyridin-2-yl)methoxy]pyridin-3-yl}methyl)-2-(1-methyl-1H-pyrazol-4-yl)pyrimidine (83.5 mg) is suspended in 25% v/v acetone (3.5 mL) solution in water at ambient temperature for two weeks. The resulting suspension is filtered, and the isolated solids are air dried to give the title compound as a crystalline solid. ES/MS m/z 419 [M+H].

EXAMPLE 5

4-({5-Methoxy-6-[(5-methoxypyridin-2-yl)methoxy]pyridin-3-yl}methyl)-2-(1-methyl-1H-pyrazol-4-yl)pyrimidine (Crystalline Form C)

Form C

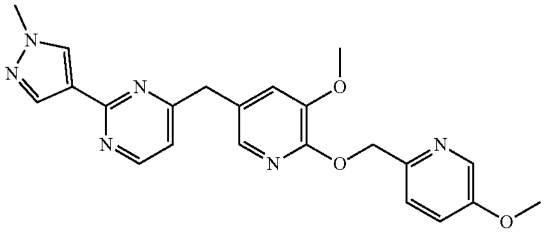

4-({5-Methoxy-6-[(5-methoxypyridin-2-yl)methoxy]pyridin-3-yl}methyl)-2-(1-methyl-1H-pyrazol-4-yl)pyrimidine (82.3 mg) is suspended in 50% v/v MeOH (2.7 mL) solution in water at ambient temperature for two weeks. The resulting suspension is filtered, and the isolated solids are air dried to give the title compound as a crystalline solid. ES/MS m/z 419 [M+H].

EXAMPLE 6

4-({5-Methoxy-6-[(5-methoxypyridin-2-yl)methoxy]pyridin-3-yl}methyl)-2-(1-methyl-1H-pyrazol-4-yl)pyrimidine (Crystalline Form D)

Form D

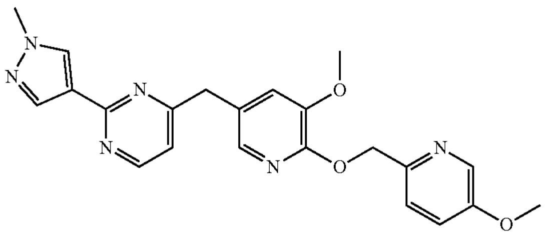

4-({5-Methoxy-6-[(5-methoxypyridin-2-yl)methoxy]pyridin-3-yl}methyl)-2-(1-methyl-1H-pyrazol-4-yl)pyrimidine (59.9 mg) is dissolved in 44% v/v THF (3.6 mL) solution in heptane at 65° C. This solution is added to excess heptane which had been cooled in an ice water bath. The resulting v/v ratio of THF to heptane is estimated at 17:83 respectively. Solids are precipitated to give a suspension which is filtered. The isolated solids are air dried to give the title compound as a crystalline solid. ES/MS m/z 419 [M+H].

EXAMPLE 7

4-({5-Methoxy-6-[(5-methoxypyridin-2-yl)methoxy]pyridin-3-yl}methyl)-2-(1-methyl-1H-pyrazol-4-yl)pyrimidine (Crystalline Form E)

Form E

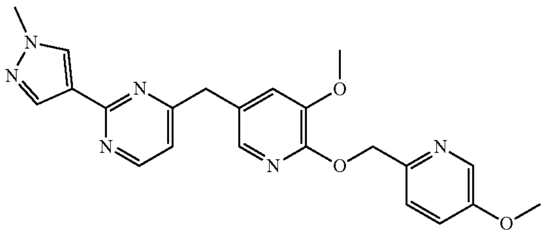

4-({5-Methoxy-6-[(5-methoxypyridin-2-yl)methoxy]pyridin-3-yl}methyl)-2-(1-methyl-1H-pyrazol-4-yl)pyrimidine (52.3 mg) is dissolved in cyclopentyl methyl ether (4 mL) at 65° C. to give a solution. The hot solution is then filtered into a glass container chilled in an ice water bath to precipitate solids. The resulting suspension is then stirred at below 0° C. temperatures overnight before the solids are isolated by filtration and air dried to give the Freebase Form E title compound as a crystalline solid. ES/MS m/z 419 [M+H].

X-Ray Powder Diffraction (XRPD) of Crystalline Forms

The XRPD patterns of crystalline solids are obtained on a Bruker D8 Endeavor X-ray powder diffractometer, a PANalytical X'Pert PRO MPD or an Empyrean diffractometer equipped with a CuKα (1.5418 Å) source and either a Linxeye detector, or an Optix long, fine-focus source operating at 40 kV and 40 mA. The sample is scanned between 4 and 42 2θ°, with a step size of 0.009 2θ° and a scan rate of 0.5 seconds/step, and using 0.3° primary slit opening, and 3.9° PSD opening. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standards with peaks at 8.853 and 26.774 2θ°. It is well known in the crystallographic art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Thus, the sample of Example 2 is characterized by an XRD pattern using CuKa radiation as having diffraction peaks (2-θ values) as described in Table 1 below. In particular, the pattern has peaks at 4.2° in combination with one or more of the peaks selected from the group consisting of 12.8°, 26.6°, 22.1° with a tolerance for the diffraction angles of 0.2 degrees.

The sample of Example 3 (Crystalline Form A) is characterized by an XRD pattern using CuKa radiation as having diffraction peaks (2-θ values) as described in Table 2 below. In particular, the pattern has peaks at 12.5° in combination with one or more of the peaks selected from the group consisting of 20.4°, 17.2°, 5.7° with a tolerance for the diffraction angles of 0.2 degrees.

The sample of Example 4 (Crystalline Form B) is characterized by an XRD pattern using CuKa radiation as having diffraction peaks (2-theta values) as described in Table 3 below. In particular, the pattern has peaks at 27.2° in combination with one or more of the peaks selected from the group consisting of 11.4°, 21.1°, 24.4° with a tolerance for the diffraction angles of 0.2 degrees.

The sample of Example 5 (Crystalline Form C) is characterized by an XRD pattern using CuKa radiation as having diffraction peaks (2-theta values) as described in Table 4 below. In particular, the pattern has peaks at 12.4° in combination with one or more of the peaks selected from the group consisting of 19.5°, 20.3°, 23.3° with a tolerance for the diffraction angles of 0.2 degrees.

The sample of Example 6 (Crystalline Form D) is characterized by an XRD pattern using CuKa radiation as having diffraction peaks (2-theta values) as described in Table 5 below. In particular, the pattern has peaks at 12.8° in combination with one or more of the peaks selected from the group consisting of 14.2°, 24.4°, 24.7° with a tolerance for the diffraction angles of 0.2 degrees.

The sample of Example 7 (Crystalline Form E) is characterized by an XRD pattern using CuKa radiation as having diffraction peaks (2-theta values) as described in Table 6 below. In particular the pattern has peaks at 23.9° in combination with one or more of the peaks selected from the group consisting of 14.2°, 24.2°, 26.0°; with a tolerance for the diffraction angles of 0.2 degrees.

TABLE 1

X-ray powder diffraction peaks of Example 2.

| Peak | Angle (°2θ) +/− 0.2° | Relative Intensity (% of most intense peak) |
|---|---|---|
| 1 | 4.2 | 100.0 |
| 2 | 12.8 | 99.5 |
| 3 | 26.6 | 89.4 |
| 4 | 22.1 | 71.6 |
| 5 | 25.7 | 62.5 |
| 6 | 23.5 | 61.1 |
| 7 | 21.3 | 56.6 |
| 8 | 23.0 | 45.4 |
| 9 | 13.9 | 45.2 |
| 10 | 20.2 | 40.2 |

TABLE 2

X-ray powder diffraction peaks of Example 3 (Crystalline Form A).

| Peak | Angle (°2θ) +/− 0.2° | Relative Intensity (% of most intense peak) |
|---|---|---|
| 1 | 12.5 | 100.0 |
| 2 | 20.4 | 15.9 |
| 3 | 17.2 | 13.2 |
| 4 | 5.7 | 11.9 |
| 5 | 13.2 | 7.5 |
| 6 | 13.7 | 6.9 |
| 7 | 18.5 | 5.9 |
| 8 | 18.2 | 5.8 |
| 9 | 8.0 | 2.6 |
| 10 | 16.1 | 2.4 |

TABLE 3

X-ray powder diffraction peaks of Example 4 (Crystalline Form B).

| Peak | Angle (°2θ) +/− 0.2° | Relative Intensity (% of most intense peak) |
|---|---|---|
| 1 | 11.4 | 74 |
| 2 | 17.8 | 42 |
| 3 | 19.1 | 39 |
| 4 | 20.3 | 37 |
| 5 | 21.1 | 93 |
| 6 | 23.6 | 57 |
| 7 | 24.1 | 54 |
| 8 | 24.4 | 100 |
| 9 | 26.2 | 79 |
| 10 | 27.2 | 100 |

TABLE 4

X-ray powder diffraction peaks of Example 5 (Crystalline Form C).

| Peak | Angle (°2 θ) +/− 0.2° | Relative Intensity (% of most intense peak) |
|---|---|---|
| 1 | 12.4 | 100 |
| 2 | 19.5 | 39 |
| 3 | 20.3 | 63 |

TABLE 4-continued

| X-ray powder diffraction peaks of Example 5 (Crystalline Form C). | | |
|---|---|---|
| Peak | Angle (°2 θ) +/− 0.2° | Relative Intensity (% of most intense peak) |
| 4 | 20.8 | 21 |
| 5 | 23.3 | 51 |
| 6 | 23.7 | 21 |
| 7 | 24.5 | 12 |
| 8 | 25.0 | 14 |
| 9 | 25.7 | 17 |
| 10 | 26.1 | 21 |

TABLE 5

| X-ray powder diffraction peaks of Example 6 (Crystalline Form D) | | |
|---|---|---|
| Peak | Angle (°2 θ) +/− 0.2° | Relative Intensity (% of most intense peak) |
| 1 | 12.8 | 100 |
| 2 | 14.2 | 65 |
| 3 | 15.1 | 32 |
| 4 | 19.7 | 35 |
| 5 | 22.5 | 62 |
| 6 | 23.4 | 49 |
| 7 | 24.4 | 96 |
| 8 | 24.7 | 60 |
| 9 | 25.4 | 49 |
| 10 | 26.0 | 45 |

TABLE 6

| X-ray powder diffraction peaks of Example 7 (Crystalline Form E) | | |
|---|---|---|
| Peak | Angle (°2 θ) +/− 0.2° | Relative Intensity (% of most intense peak) |
| 1 | 8.2 | 36 |
| 2 | 13.9 | 35 |
| 3 | 14.2 | 67 |
| 4 | 18.1 | 42 |
| 5 | 18.3 | 42 |
| 6 | 20.8 | 45 |
| 7 | 23.9 | 100 |
| 8 | 24.2 | 85 |
| 9 | 26.0 | 92 |
| 10 | 27.5 | 59 |

Biological Assays hCSF-1R Binding Assay

Serial dilutions of the test compounds are prepared in DMSO resulting in a 3-fold dilution to yield a 10-point response curve. The 10-point compound titration (15 nL) is added to each well in rows A-P and columns 3-12 and 13-22 of the corresponding assay plate (ProxiPlate™-384 Plus F, Black) using acoustic dispensing. DMSO (15 nL) is then added to rows A-P, columns 1-2 and 23-24 as assay controls. Assay buffer (HEPES 62.5 mM, pH 7.5, 0.01% Brij™ 35, 12.5 $MgCl_2$ and 1.25 mM EGTA) is used to prepare all assay reagents. The CSF-1R LanthaScreen™ Eu Kinase Binding Assay is run essentially as recommended by the vendor (LanthaScreen™ Eu Kinase Binding Assay Validation Packet, Invitrogen). A solution (7.5 μL) containing LanthaScreen™ Eu-anti-His Antibody (PV5596, Thermo Fisher) and Kinase Tracer 236 (PV5592, Thermo Fisher) is added to the entire plate resulting in a final concentration of 2 nM and 200 nM, respectively. Recombinant human CSF-1R (7.5 μL, aa 538-919, expressed in a Baculovirus expression system) is then added to rows A-P, columns 1-22 resulting in a final enzyme concentration of 5 nM. Assay buffer (7.5 μL) is added to columns 23 and 24. The assay plates are briefly shaken, incubated for 1 hour at RT, and read on a plate reader using the appropriate filters and instrument settings for europium-based LanthaScreen™ assays (Excitation 340 nm, Emission 665 nm, Emission 615 nm, delay time 100 μs). The emission ratio (665/615) is calculated for each well and relative activity is determined based on column 1 and 2 (100% activity) and columns 23 and 24 (0% activity). The 10-point response curves are plotted and fitted with the 4-parameter logistic equation to obtain the $IC_{50}$ values. Example 1 shows an $IC_{50}$ of 80.47 nM±15.53, n=6. The data shows that Example 1 is active against recombinant, truncated CSF-1R in a kinase binding assay.

DiscoverX® PathHunter Receptor Tyrosine Kinase (RTK) Cell Based Functional Assay For in vitro PDGFRβ (Accession NM_002609, Part No. 93-0493C3) and c-Kit (Accession NM_000222, Part No. 93-0853C3) cellular assays, the test compounds are prepared in DMSO to make up a 10 mM stock solution. The stock solution is serially diluted two-fold in DMSO to obtain a twenty-point curve with final compound concentrations ranging from 20.0 μM to 0.019 nM.

DiscoverX® PathHunter Receptor Tyrosine Kinase (RTK) cell based functional assays are utilized to profile compounds using Enzyme Fragment Complementation technology with human PDGFRβ U2OS cells and human c-Kit U2OS cells. Cells are continuously cultured from cell passage 5 up to cell passage 30 in AssayComplete™ Cell Culture Kit-103 (DiscoverX®, 92-3103G) media containing 500 μg/mL G418 and 250 μg/mL hygromycin. PDGFRβ or c-Kit cells (27 μL) in media (DiscoverX®, 93-0563R16B) are seeded at $1.5\times10^4$ cells/well into all wells of a Corning 384 poly-d-lysine coated white plate. The cell plates are then incubated overnight at 37° C., 5.0% $CO_2$. Compound serial dilutions are then added to rows A-P, columns 3-22. DMSO and inhibitor controls are added to rows A-P, columns 1-2 and 23-24, respectively. Cell plates with compound or controls are incubated for 1 hour at 37° C., 5.0% $CO_2$. After incubation, an EC80 dose of 3 nM recombinant human PDGF-BB (Catalog #100-14B) or 10 nM recombinant Human Stem Cell Factor (DiscoverX®, #300-07) agonist are stamped onto the corresponding PDGFRβ or c-Kit cell plates and incubated for 3 hours at 23° C., 5.0% $CO_2$. Chemiluminescent Reagent (DiscoverX®, #93-0001XL) is then added to each cell plate and incubated for 1 hour at RT. After 1 hour, cell plates are read on a chemiluminescence capable plate reader. The 20-point curves are plotted and fitted with the 4-parameter logistic equation to obtain the $IC_{50}$ values based on activity of each well relative to inhibitor (0% activity) and DMSO (100% activity) control wells. Example 1 shows an $IC_{50}$ of >20,000 nM, n=4 and 5,615 nM±881, n=4 versus PDGFRβ and c-Kit, respectively. The data shows that Example 1 does not have pharmacologically relevant activity with respect to PDGFRβ or c-Kit compared to hCSF-1R.

DiscoverX® KINOMEscan™ In Vitro Kinase Competition Binding Assay

The KINOMEscan™ screening platform employs a novel and proprietary active site-directed competition binding assay to quantitatively measure interactions between a test compound and more than 450 human kinases and disease relevant mutant variants. KINOMEscan™ assays do not require ATP and thereby report true thermodynamic interaction affinities. Compounds that bind the kinase active site and directly (sterically) or indirectly (allosterically) prevent kinase binding to an immobilized ligand will reduce the amount of kinase captured on the solid support. However, compounds that do not bind the kinase have no effect on the amount of kinase captured on the solid support. Compound activity (% binding) is monitored by measuring the amount of kinase captured in test versus control samples by using a qPCR method that detects the associated DNA label. The binding activity is converted to % inhibition and an $IC_{50}$ value is determined for CSF-1R fold-selectivity assessment.

Assays to monitor binding to a 468-kinase panel are conducted at DiscoverX® Corporation (Fremont, CA). Test compound is provided as a 10 mM stock in 100% DMSO and evaluated at 20 nM, 2 nM and 0.2 nM final concentrations. Kinases are tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (Pierce SeaBlock, 1% BSA, 0.05% Tween 20 and 1 mM DTT) to remove unbound ligand and to reduce nonspecific binding. Binding reactions are assembled by combining kinases, liganded affinity beads, and test compound in 1×binding buffer (20% Pierce SeaBlock, 0.17×PBS, 0.05% Tween 20 and 6 mM DTT). Test compound is prepared as a 40×stock in 100% DMSO and directly diluted into the assay. All reactions are performed in polypropylene 384-well plates in a final volume of 0.02 mL. The assay plates are incubated at room temperature with shaking for 1 hour and the affinity beads are washed with wash buffer (1×PBS and 0.05% Tween 20). The beads are then re-suspended in elution buffer (1×PBS, 0.05% Tween 20 and 0.5 μM non-biotinylated affinity ligand) and incubated at room temperature with shaking for 30 minutes. The kinase concentration in the eluates is measured by qPCR. The results for primary screen binding interactions are reported as '% Ctrl', where lower numbers indicate stronger hits in the matrix.

Percent of control (% Ctrl) calculation:

$$\left(\frac{\text{test compound signal} - \text{positive control signal}}{\text{negative control signal} - \text{positive control signal}}\right)\times 100$$

test compound=compound submitted by Eli Lilly and Company negative control=DMSO (100% Ctrl)

positive control=control compound (0% Ctrl)

The percent inhibition values, and the 3-point concentration response data are subsequently determined and analyzed with NGR software, and non-standard $IC_{50}$ values are calculated from the resulting curve fit. 3 log units of maximal extrapolation range is used to ensure that NSIC50 is not masked on the selected range. Also, the minimal number of valid points is equal to 3.

Fit Model: Hill Fit

4 Parameter Logistic Model or Sigmoidal Dose-Response Model.

$$fit=(A+((B-A)/(1+((C/x)\hat{}D))))$$

$$inv=(C/((((B-A)/(y-A))-1)\hat{}(1/D)))$$

$$res=(y-fit)$$

Where A=bottom fixed to zero

Where B=top fixed to 100

Where C=potency

Where D=hill fixed to 1

From the $IC_{50}$ values, compound fold-selectivity for CSF-1R in relationship to the other kinases is determined. The data shows that Example 1 has excellent selectivity against the 468 protein kinases in the panel with only 3 kinases showing less than 35% control activity (or >65% inhibition) at the 2 μM compound concentration (CSF1R 99%, CSF1R autoinhibited 98.9%, KIT 99.4%, KIT V559D 99.5%, KIT L576P 96.4%, KIT V559D V654A 84% and PDGFRB 90.8% inhibition). The data also shows that Example 1 has >1000-fold selectivity for CSF-1R in relationship to all the kinases in the panel, except for the following: hKIT (62-fold selective), hPDGFRβ (258-fold selective), and hTRKB (700-fold selective). In addition, the hKIT mutants V559D, V559D V654A and L576P showed 59- to 500-fold selectivity for CSF-1R.

pCSF-1R Cell Imaging Assay

Human CSF-1R over-expressing NIH-3T3 cells (internally generated cell line, clone H2S-25-20) are grown in a T225 tissue culture flask with DMEM media (50 mL) supplemented with 10% FBS. Cells are plated onto a 384-well poly-d-lysine coated black plate at 5,000 cells/well using serum-free DMEM media. The cell stock solution is at $1.67\times10^5$ cells/mL and a 30 μl plating volume is used. The plates are incubated at RT for 0.5 hour and then at 37° C., 5% $CO_2$ overnight. The cells are treated with compound (6 μl of 6×serially diluted stock solutions) dissolved in serum-free DMEM containing 0.1% DMSO and incubated for 2 hours at 37° C. Recombinant human M-CSF (4 μl of 200 ng/mL stock solution, expressed in *E. coli* using a T7 RNA polymerase-IPTG induction system) is added in serum free DMEM media. The plates are centrifuged for 1 minute at 1,000×g immediately after adding M-CSF stimulant. The plates are incubated for 20 minutes at 37° C. The cells are fixed with fresh 16% paraformaldehyde (12 μl) and the plates are incubated for 30 minutes at RT. The paraformaldehyde is removed, and PBS (30 μl) is added. The PBS is removed, and PBS (30 μl) supplemented with 0.1% triton-100 is added. The plates are incubated at RT for 20 minutes. The plates are washed with PBS (2×50 μl/well). Primary antibody, rabbit anti-pCSF-1R (6.4 mg/mL, Invitrogen, catalog #MA5-15151, Phospho-CSF1R (Tyr723) monoclonal antibody (F.540.2)) diluted 1:9,000 in PBS supplemented with 1% BSA (30 μl/well) is added and the plates are incubated at RT for 2 hours. The plates are washed with PBS (2×50 μl/well). Secondary antibody, anti-rabbit-Alexa488 (Invitrogen, #A11034) diluted 1:1,000 in PBS (30 μl/well) is added. The plates are washed with PBS (2×50 μl/well). Nuclear stain, propidium iodide (2 μg/ml) mixed with RNase (50 μg/ml) in PBS, is added (30 μl/well) and the plates are sealed with black tape for pCSF-1R imaging on the Acumen instrument. The 10-point compound curves are plotted and fitted with the 4-parameter logistic equation to obtain the $IC_{50}$ values based on the activity of each well relative to a reference CSF-1R inhibitor (PLX3397, Plexicon, 0% activity) and DMSO (100% activity) control wells. Example 1 shows an $IC_{50}$ of 52.31 nM±18.14, n=4. The data shows that Example 1 is active against endogenous, full-length CSF-1R in a cell-based CSF-1R phosphorylation imaging assay.

I claim:

1. A compound of the formula:

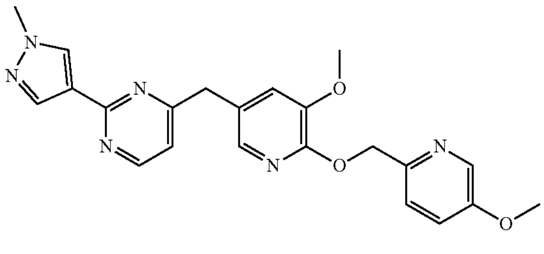 [SMILES: COc1ccc(COc2ncc(Cc3ccnc(-c4cnn(C)c4)n3)cc2OC)nc1]

or a pharmaceutically acceptable salt thereof.

2. A method of treating Alzheimer's disease in a patient in need thereof, comprising administering to the patient an effective amount of the compound of claim 1, or a pharmaceutically acceptable salt thereof.

3. A pharmaceutical composition, comprising an effective amount of the compound, or a pharmaceutically acceptable salt thereof, of claim 1 and one or more pharmaceutically acceptable carrier, diluent, or excipient.

4. A process for preparing a pharmaceutical composition, comprising admixing the compound, or a pharmaceutically acceptable salt thereof, of claim 1 with one or more pharmaceutically acceptable carrier, diluent, or excipient.

5. A compound of the formula:

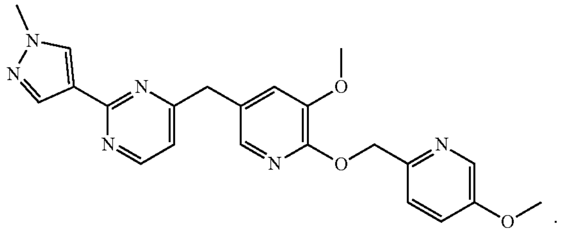 [SMILES: COc1ccc(COc2ncc(Cc3ccnc(-c4cnn(C)c4)n3)cc2OC)nc1]

6. A pharmaceutical composition comprising an effective amount of the compound of claim 5 and one or more pharmaceutically acceptable carrier, diluent, or excipient.

7. A process for preparing a pharmaceutical composition, comprising admixing the compound of claim 5 with one or more pharmaceutically acceptable carriers, diluents, or excipients.

8. A method of treating Alzheimer's disease in a patient in need thereof, comprising administering to the patient an effective amount of the compound of claim 5.

* * * * *